(12) United States Patent
Tsuda

(10) Patent No.: US 8,252,231 B2
(45) Date of Patent: Aug. 28, 2012

(54) ANALYZER AND ITS ABNORMALITY COPING METHOD

(75) Inventor: Nobuyoshi Tsuda, Hino (JP)

(73) Assignee: Beckman Coulter, Inc., Brea, CA (US)

( * ) Notice: Subject to any disclaimer, the term of this patent is extended or adjusted under 35 U.S.C. 154(b) by 319 days.

(21) Appl. No.: 12/687,609

(22) Filed: Jan. 14, 2010

(65) Prior Publication Data

US 2010/0112704 A1   May 6, 2010

Related U.S. Application Data

(63) Continuation of application No. PCT/JP2008/062606, filed on Jul. 11, 2008.

(30) Foreign Application Priority Data

Jul. 18, 2007   (JP) ................................. 2007-187051

(51) Int. Cl.
B01F 11/02 (2006.01)
G01N 25/72 (2006.01)

(52) U.S. Cl. .............. 422/62; 366/114; 374/45; 436/50; 73/1.02

(58) Field of Classification Search ........................ None
See application file for complete search history.

(56) References Cited

U.S. PATENT DOCUMENTS

| | | | |
|---|---|---|---|
| 6,875,401 B1 * | 4/2005 | Suzuki et al. ................... | 422/63 |
| 8,092,079 B2 * | 1/2012 | Misu ............................... | 374/45 |
| 2005/0150830 A1 * | 7/2005 | Laugharn et al. ............. | 210/634 |
| 2006/0148063 A1 * | 7/2006 | Fauzzi et al. ................ | 435/286.4 |
| 2008/0141784 A1 * | 6/2008 | Murakami ................. | 73/861.18 |
| 2009/0092518 A1 * | 4/2009 | Murakami ................. | 422/82.05 |
| 2010/0135352 A1 * | 6/2010 | Tsuda ............................. | 374/45 |

FOREIGN PATENT DOCUMENTS

| | | |
|---|---|---|
| EP | 1 260 819 A1 | 11/2002 |
| EP | 1 795 822 A1 | 6/2007 |
| JP | 2001-013149 A | 1/2001 |

(Continued)

OTHER PUBLICATIONS

Chen, J. et al. "Study of anisotropic etching of (1 0 0) Si with ultrasonic agitation," Sensors and Actuators A: Physical 96 (2002) 152-156.*

(Continued)

*Primary Examiner* — Yelena G Gakh
*Assistant Examiner* — Michelle Adams
(74) *Attorney, Agent, or Firm* — Kilpatrick Townsend & Stockton LLP

(57) ABSTRACT

An analyzer includes plural stirrers that have plural sound-wave generating units, which are provided on respective vessels holding liquid and generate sound wave toward the liquid, and drive units, which drive the plurality of sound-wave generating units, and that stir the liquid using sound wave generated by the sound-wave generating units; a power detecting unit that detects traveling-wave power output from the drive unit and reflected-wave power reflected from the sound-wave generating unit; and a control unit that determines whether an abnormality occurs in each of the stirrers on the sound-wave generating unit side or on the drive unit side in each of the stirrers based on a reflectivity of the power, and controls continuation or suspension of an analytical work based on a result of the determination.

6 Claims, 8 Drawing Sheets

FOREIGN PATENT DOCUMENTS

| | | |
|---|---|---|
| JP | 2004-184141 A | 7/2004 |
| JP | 2006-119125 A | 5/2006 |
| WO | WO 01/63300 A1 | 8/2001 |
| WO | WO 2006/033307 A1 | 3/2006 |

OTHER PUBLICATIONS

English Translation of International Search Report from PCT/JP2006/062606 dated Sep. 22, 2008 (4 pages in both English and Japanese).

* cited by examiner

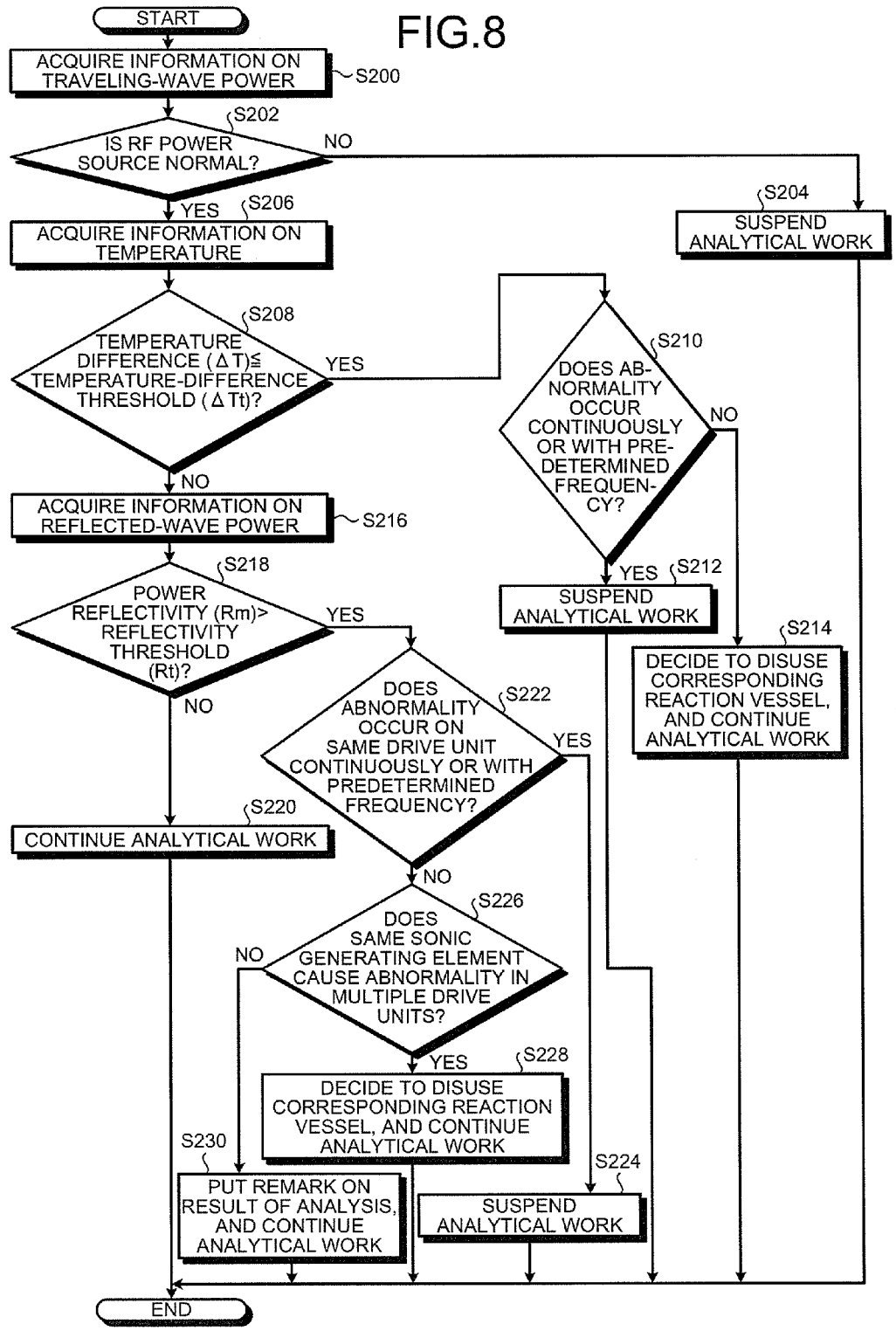

ANALYZER AND ITS ABNORMALITY COPING METHOD

CROSS-REFERENCE TO RELATED APPLICATIONS

This application is a continuation of PCT international application Ser. No. PCT/JP2008/062606 filed on Jul. 11, 2008 which designates the United States, incorporated herein by reference, and which claims the benefit of priority from Japanese Patent Application No. 2007-187051, filed on Jul. 18, 2007, incorporated herein by reference.

BACKGROUND OF THE INVENTION

1. Field of the Invention

The present invention relates to an analyzer and its abnormality coping method.

2. Description of the Related Art

Conventionally, an analyzer analyzes the concentration and the like of a specific component in a specimen by measuring an optical property of a reaction liquid produced by reaction of a reagent and the specimen. To perform a high-precision analysis while avoiding so-called carry-over, the analyzer is equipped with a stirrer for stirring the reagent and specimen or these mixture using sound wave in a non-contact manner (for example, see Japanese Patent Application Laid-open No. 2006-119125). The stirrer stirs liquid held in a vessel using sound wave that is generated by driving a sound-wave generating element.

SUMMARY OF THE INVENTION

According to an aspect of the present invention, there is provided an analyzer including a plurality of stirrers that have a plurality of sound-wave generating units, which are provided on respective vessels holding liquid and generate sound wave toward the liquid, and drive units, which drive the plurality of sound-wave generating units, and that stir the liquid using sound wave generated by the sound-wave generating units; a power detecting unit that detects traveling-wave power output from the drive unit and reflected-wave power reflected from the sound-wave generating unit; and a control unit that determines whether an abnormality occurs in each of the stirrers on the sound-wave generating unit side or on the drive unit side in each of the stirrers based on a reflectivity of the power, and controls continuation or suspension of an analytical work based on a result of the determination.

According to another aspect of the present invention, there is provided a method for coping with an abnormality of an analyzer that includes a plurality of stirrers that have a plurality of sound-wave generating units, which are provided on respective vessels holding liquid and generate sound wave toward the liquid, and drive units, which drives the plurality of sound-wave generating units individually, and that stir the liquid using sound wave generated by the sound-wave generating units, the method including a power detecting step of detecting traveling-wave power output from the drive unit and reflected-wave power reflected from the sound-wave generating unit; and a control step of determining whether an abnormality occurs in each of the stirrers on the sound-wave generating unit side or on the drive unit side based on a reflectivity of the power and controlling continuation or suspension of an analytical work based on a result of the determination.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 8 is a flowchart illustrating a method for coping with an abnormality of the automatic analyzer according to the second embodiment.

DETAILED DESCRIPTION OF THE PREFERRED EMBODIMENTS

First Embodiment

Figure 1:
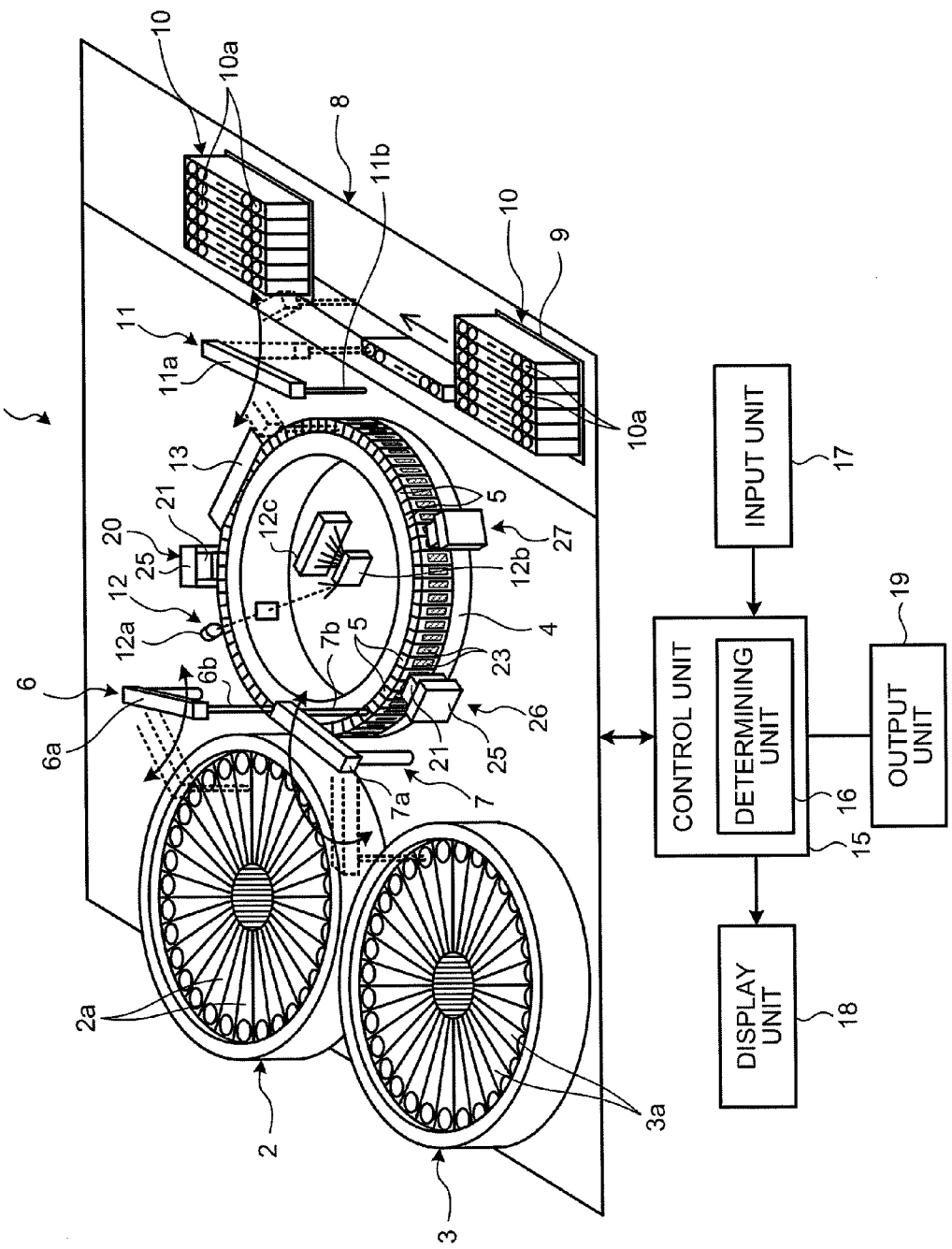
FIG. 1 is a schematic configuration diagram illustrating an automatic analyzer according to a first embodiment.
Figure 2:
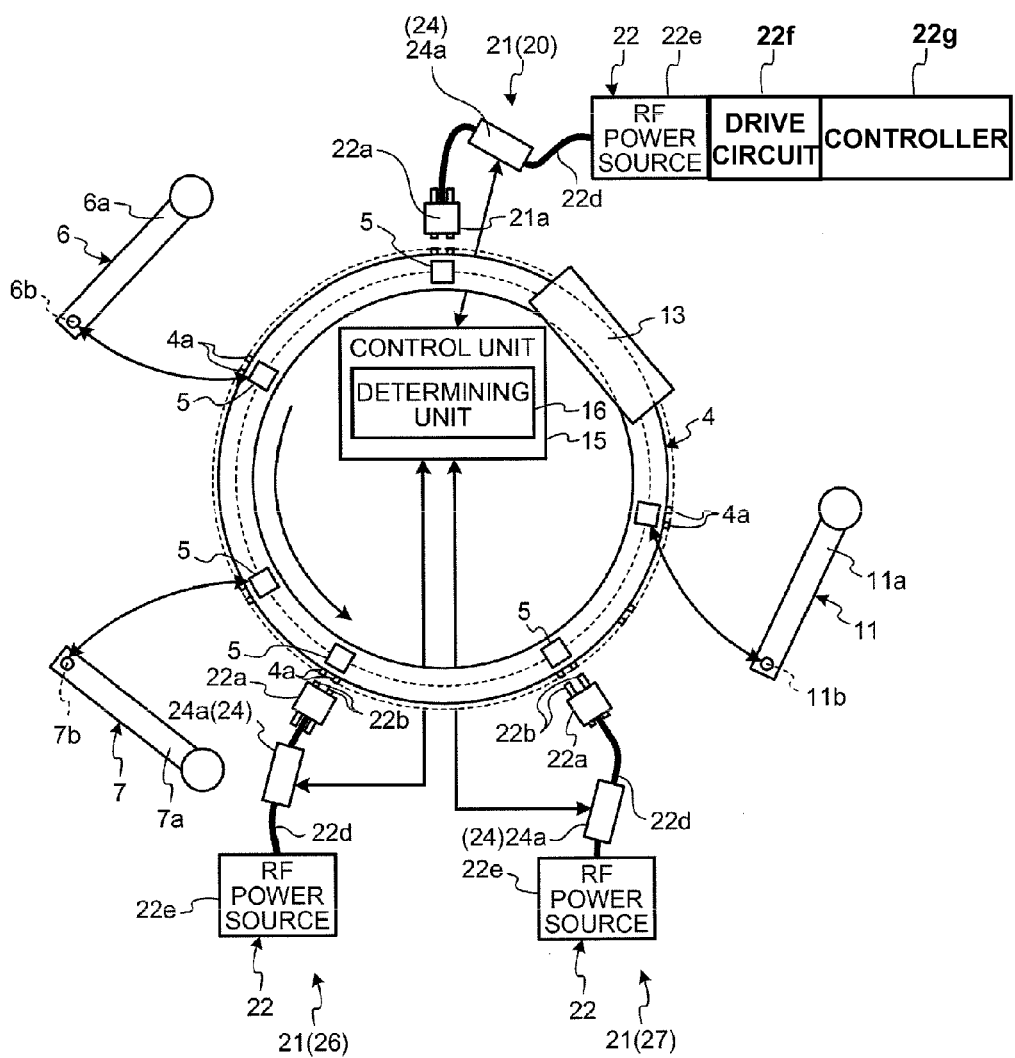
FIG. 2 is a plan view illustrating a reagent dispensing system, a specimen dispensing system, a specimen stirrer, and a reagent stirrer that are arranged near a reaction table in the automatic analyzer according to the first embodiment.
Figure 3:
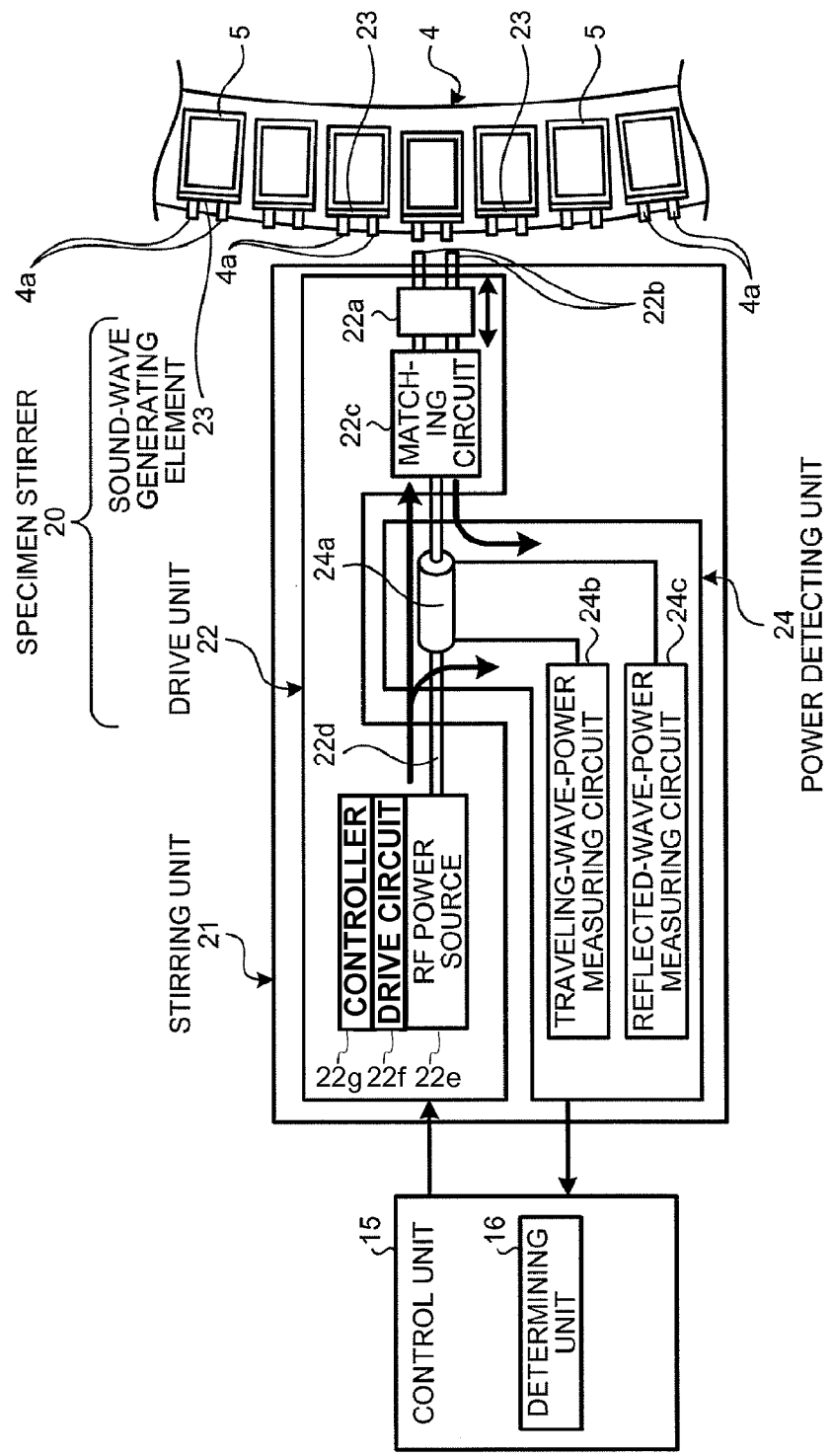
FIG. 3 is a diagram explaining the power transmission to a sound-wave generating element mounted on a reaction vessel and explaining the detection of a connection status of a drive unit and the sound-wave generating element in a stirrer, which has the drive unit and the sound-wave generating element, in the automatic analyzer according to the first embodiment.

A first embodiment of an analyzer and its abnormality coping method of the present invention will be described in detail below with reference to the accompanying drawings. FIG. 1 is a schematic configuration diagram illustrating an automatic analyzer according to the first embodiment. FIG. 2 is a plan view illustrating a reagent dispensing system, a specimen dispensing system, a specimen stirrer, and a reagent stirrer that are arranged near a reaction table in the automatic analyzer according to the first embodiment. FIG. 3 is a diagram explaining the power transmission to a sound-wave generating element mounted on a reaction vessel and explaining the detection of a connection status of a drive unit and the sound-wave generating element in a stirrer, which has the drive unit and the sound-wave generating element, in the automatic analyzer according to the first embodiment.

As shown in FIGS. 1 and 2, an automatic analyzer 1 includes reagent tables 2 and 3, a reaction table 4, a specimen-vessel transfer system 8, an analysis optical system 12, a cleaning system 13, a control unit 15, a specimen stirrer 20, a power detecting unit 24, and reagent stirrers 26 and 27.

The reagent tables 2 and 3 are each rotated by a drive means, and as shown in FIG. 1, convey reagent vessels 2a each holding a first reagent and reagent vessels 3a each holding a second reagent in a circumferential direction, respectively.

As shown in FIGS. 1 and 2, a plurality of reaction vessels 5 are arranged on the reaction table 4 along a circumferential direction. The reaction table 4 rotates while keeping the reaction vessels 5 at a predetermined temperature, for example, at 37° C., and conveys the reaction vessels 5 along the circumferential direction. On the outer surface of the reaction table 4 where each of the reaction vessels 5 is arranged, connection terminals 4a that establish connections to sound-wave generating elements 23 are provided along the circumferential direction. The reaction table 4 rotates, for example, (one revolution subtracted by one reaction vessel)/4 revolution in one cycle, and rotates (one revolution subtracted by one reaction vessel) revolution through four cycles. Reagent dispensing systems 6 and 7, a specimen dispensing system 11, the specimen stirrer 20, and the reagent stirrers 26 and 27 are arranged near the reaction table 4.

The reaction vessel 5 is a cuvette that has a minute capacity of a few µL to a few hundred µL, and is made of a transparent material capable of letting through over 80% of a light contained in an analysis light emitted from a light-emitting unit 12a of the analysis optical system 12, e.g., glass including heat resistance glass, synthetic resin such as cyclic olefin and polystyrene. The sound-wave generating element 23 that forms the stirrer 20 is mounted on a side wall of the reaction vessel 5. The reaction vessel 5 is arranged on the reaction table 4 so that the sound-wave generating element 23 is faced outward in a radial direction. The reagents are dispensed from the reagent vessels 2a and 3a into the reaction vessels 5 by the reagent dispensing systems 6 and 7 provided near the outer circumference of the reaction table 4.

In the reagent dispensing systems 6 and 7, probes 6b and 7b for dispensing the reagent are provided on respective arms 6a and 7a that each turn in a direction of arrow in the horizontal plane. The reagent dispensing systems 6 and 7 each include a probe cleaning unit for cleaning the corresponding probe 6b or 7b with cleaning water.

As shown in FIG. 1, the specimen-vessel transfer system 8 transfers a plurality of racks 10 aligned on a feeder 9 by moving step by step along a direction of arrow. The rack 10 holds a plurality of specimen vessels 10a each housing a specimen. Each time the step-by-step movement of the racks 10 transferred by the specimen-vessel transfer system 8 is stopped, the specimen in the specimen vessel 10a is dispensed into the reaction vessel 5 by the specimen dispensing system 11 that has a drive arm 11a capable of turning in a horizontal direction and a probe 11b. The specimen dispensing system 11 includes a probe cleaning unit for cleaning the probe 11b with cleaning water.

The analysis optical system 12 emits an analysis light for analyzing liquid in the reaction vessel 5, which is produced by reaction of the reagent and the specimen, and, as shown in FIG. 1, includes the light-emitting unit 12a, a light-splitting unit 12b, and a light-receiving unit 12c. An analysis light emitted from the light-emitting unit 12a goes through the liquid in the reaction vessel 5, and is received by the light-receiving unit 12c provided at the position opposed to the light-splitting unit 12b. The light-receiving unit 12c is connected to the control unit 15 and outputs a light-amount signal of the received analysis light to the control unit 15.

The cleaning system 13 cleans the reaction vessel 5, which has undergone the light measurement, and includes a suction nozzle for sucking reaction liquid and detergent or cleaning water from the reaction vessel 5 and a dispensing nozzle for dispensing detergent or cleaning water. After sucking reaction liquid, for which the light measurement has completed, from the reaction vessel 5, the cleaning system 13 dispenses detergent or cleaning water. By repeating the dispensing and sucking of detergent or cleaning water plural times, the cleaning system 13 cleans the reaction vessel 5. The reaction vessel 5 thus cleaned is again used for the analysis of a new specimen.

A microcomputer or the like is used as the control unit 15, for example. The control unit 15 is connected to each of units of the automatic analyzer 1, and controls the operation of each of these units. The control unit 15 analyzes the concentration of a component of the specimen or the like on the basis of an absorbance of the liquid in the reaction vessel 5 based on an amount of light emitted by the light-emitting unit 12a and an amount of light received by the light-receiving unit 12c. The control unit 15 executes the analysis while controlling the operation of each of the units of the automatic analyzer 1 in accordance with an analysis command input through an input unit 17 such as a keyboard. The control unit 15 causes a display unit 18 such as a display panel to display a result of the analysis and warning information for announcing an abnormality of the stirrer as well as various information in accordance with a display command input through the input unit 17. The control unit 15 outputs information including the analysis result and the warning information by printing the information on a recording paper sheet or the like through an output unit 19 such as a printer. Furthermore, the control unit 15 controls the start or suspension of an analytical work based on the presence or absence of an abnormality of each of the stirrers determined by a determining unit 16.

The determining unit 16 determines the presence or absence of an abnormality in each of the stirrers based on a reflectivity of the electric power in each of the specimen stirrer 20 and the reagent stirrers 26 and 27 that is detected by the power detecting unit 24.

The specimen stirrer 20 and the reagent stirrers 26 and 27 each stir liquid held in the reaction vessel 5, such as a specimen or a reagent, in a non-contact manner using sound wave generated by driving the sound-wave generating element 23, and include a drive unit 22 and the sound-wave generating elements 23. As shown in FIGS. 2 and 3, the drive unit 22 is integrated in a stirring unit 21 together with the power detecting unit 24. The specimen stirrer 20 and the reagent stirrers 26 and 27 have the same configuration. Thus, the specimen stirrer 20 is explained, and the detailed explanation of the reagent stirrers 26 and 27 is omitted by using corresponding reference numerals to the corresponding components.

The stirring units 21 are arranged at the positions opposed to one another on the outer circumference of the reaction table 4 so as to be opposed to the reaction vessels 5 in the horizontal direction, and each transmits the electric power supplied from a radio-frequency alternating-current source of about a few MHz to a few hundred MHz to the sound-wave generating element 23. As shown in FIGS. 2 and 3, the stirring unit 21 includes the drive unit 22 and the power detecting unit 24.

As shown in FIGS. 2 and 3, the drive unit 22 includes a solenoid 22a, a matching circuit 22c, and a radio-frequency (RF) power source (hereinafter, referred to as "RF power source") 22e as well as a drive circuit 22f and a controller 22g. In the drive unit 22, as shown in FIG. 3, the matching circuit 22c and the RF power source 22e are connected by a coaxial cable 22d that has a characteristic impedance of 50Ω. A connection terminal 22b is brought into contact with the connection terminal 4a provided on the outer surface of the reaction table 4 by the solenoid 22a in order to drive the sound-wave generating element 23. The matching circuit 22c adjusts a load of the sound-wave generating element 23, the load viewed from the RF power source 22e, to be 50Ω.

As shown in FIG. 1, the stirring unit 21 is supported by a positioning member 25. The stirring unit 21 transmits the electric power to the connection terminal 4a through the connection terminal 22b when the rotation of the reaction table 4 is stopped to stir liquid held in the reaction vessel 5, such as a specimen or a reagent, using sound wave generated by the sound-wave generating element 23.

The sound-wave generating element 23 is, for example, configured such that an oscillator composed of a plurality of comb electrodes (Interdigital Transducers)(IDTs) is provided on one surface of a piezoelectric substrate made of lithium niobate (LiNbO3). The element 23 is mounted on the side wall of the reaction vessel 5 via an acoustic matching layer, such as epoxy resin or ultraviolet curable resin. When the rotation of the reaction table 4 is stopped, the sound-wave generating element 23 is connected to the drive unit 22 via the connection terminal 4a and stirs liquid held in the reaction vessel 5, such as a specimen or a reagent, in a non-contact manner.

The power detecting unit 24 detects traveling-wave power output from the drive unit 22 and reflected-wave power reflected from the sound-wave generating element 23. The unit 24 includes a directional coupler 24a, a traveling-wave-power measuring circuit 24b, and a reflected-wave-power measuring circuit 24c. The directional coupler 24a is provided on the coaxial cable 22d that connects the matching circuit 22c and the RF power source 22e. The traveling-wave-power measuring circuit 24b measures the electric power of one of traveling waves that are output from the RF power source 22e and separated thereinto by the directional coupler 24a. The other traveling wave is output to the sound-wave generating element 23 via the matching circuit 22c and the connection terminal 22b. The reflected-wave-power measuring circuit 24c measures the electric power of a reflected wave reflected from the sound-wave generating element 23. Information on the traveling-wave power and the reflected-wave power measured by the traveling-wave-power measuring circuit 24b and the reflected-wave-power measuring circuit, respectively, 24c is output to the determining unit 16. The presence or absence of an abnormality of each stirrer is determined based on a reflectivity of the reflected-wave power with respect to the traveling-wave power. This presence or absence of an abnormality includes the presence or absence of an abnormality of the RF power source 22e that is determined based on traveling-wave power.

An abnormality determined by the determining unit 16 is mainly an abnormality in connection. Abnormalities can be categorized into an abnormality on the side of the drive unit 22 and an abnormality on the side of the sound-wave generating element 23. Abnormalities of the drive unit 22 side includes an abnormality of the RF power source 22e, a malfunction of the matching circuit 22c, short-circuiting or breaking of the coaxial cable 22d, an abnormality in the connection between the connection terminal 22b and the connection terminal 4a. Abnormalities of the sound-wave generating element 23 side includes a bad connection between the connection terminal 4a and the sound-wave generating element 23, short-circuiting or breaking of the comb electrode of the sound-wave generating element 23, an abnormality inducing an impedance change caused by the adhesion of water or an elastic body to the sound-wave generating element 23.

In the determination of an abnormality, a predetermined threshold may be decided in advance. When a power reflectivity (Rm), which is a ratio between traveling-wave power and reflected-wave power, exceeds a reflectivity threshold (Rt=10%), it may be determined that there is an abnormality. An abnormality may be on the side of the drive unit 22 or on the side of the sound-wave generating element 23, but when the same sound-wave generating element 23 is abnormal over plural drive units 22, it may be determined that the abnormality is on the side of this specific sound-wave generating element 23. On the contrary, when the same drive unit 22 is abnormal over plural sound-wave generating elements 23, it may be determined that the abnormality is on the side of this specific drive unit 22.

There is a variation in impedance of the matching circuit 22c or the sound-wave generating element 23. Thus, a predetermined threshold may be decided in advance, and the determining unit 16 may determine that the traveling-wave power and the connection between the connection terminal 22b of the drive unit 22 and the connection terminal 4a are abnormal, and thus the stirrer is abnormal. Furthermore, a reflectivity of each of the stirrers in the normal operation may be preliminarily measured with respect to each of the reaction vessels 5 and stored as a reference reflectivity (Rs) in the determining unit 16. When $\Delta R(=Rm-Rs)$, which is a difference of reflectivity between a reflectivity (Rm) measured at the time of analysis and the reference reflectivity, exceeds a predetermined reflectivity threshold (Rt), for example, 5% of the reference reflectivity (Rs) ($\Delta R > \Delta Rt = 0.05\ Rs$), the determining unit 16 may determine that the connection between the connection terminal 22b of the drive unit 22 and the sound-wave generating element 23 is abnormal, and thus the stirrer is abnormal.

The positioning member 25 adjusts the relative position of the stirring unit 21 and the connection terminal 4a in the circumferential direction and the radial direction of the reaction table 4 by moving the stirring unit 21 at the time of power transmission, at which the electric power is transmitted from the stirring unit 21 to the connection terminal 4a.

The automatic analyzer 1 configured as described above operates under the control of the control unit 15. The first reagent, the second reagent, and the specimen are sequentially dispensed into the reaction vessels 5, which are conveyed along the circumferential direction by the rotating reaction table 4, by the reagent dispensing systems 6 and 7 and the specimen dispensing system 11, respectively. The dispensed reagents and specimen are stirred by the reagent stirrers 26 and 27 and the specimen stirrer 20 sequentially.

Then, when each of the reaction vessels 5 in which the reagents and the specimen have been stirred passes through the analysis optical system 12, an optical property of a reaction liquid is measured in the light-receiving unit 12c, and the component concentration and the like are analyzed by the control unit 15. The reaction vessel 5 that has undergone the light measurement of the reaction liquid is cleaned by the cleaning system 13, and then used for analysis of a specimen again.

Figure 4:
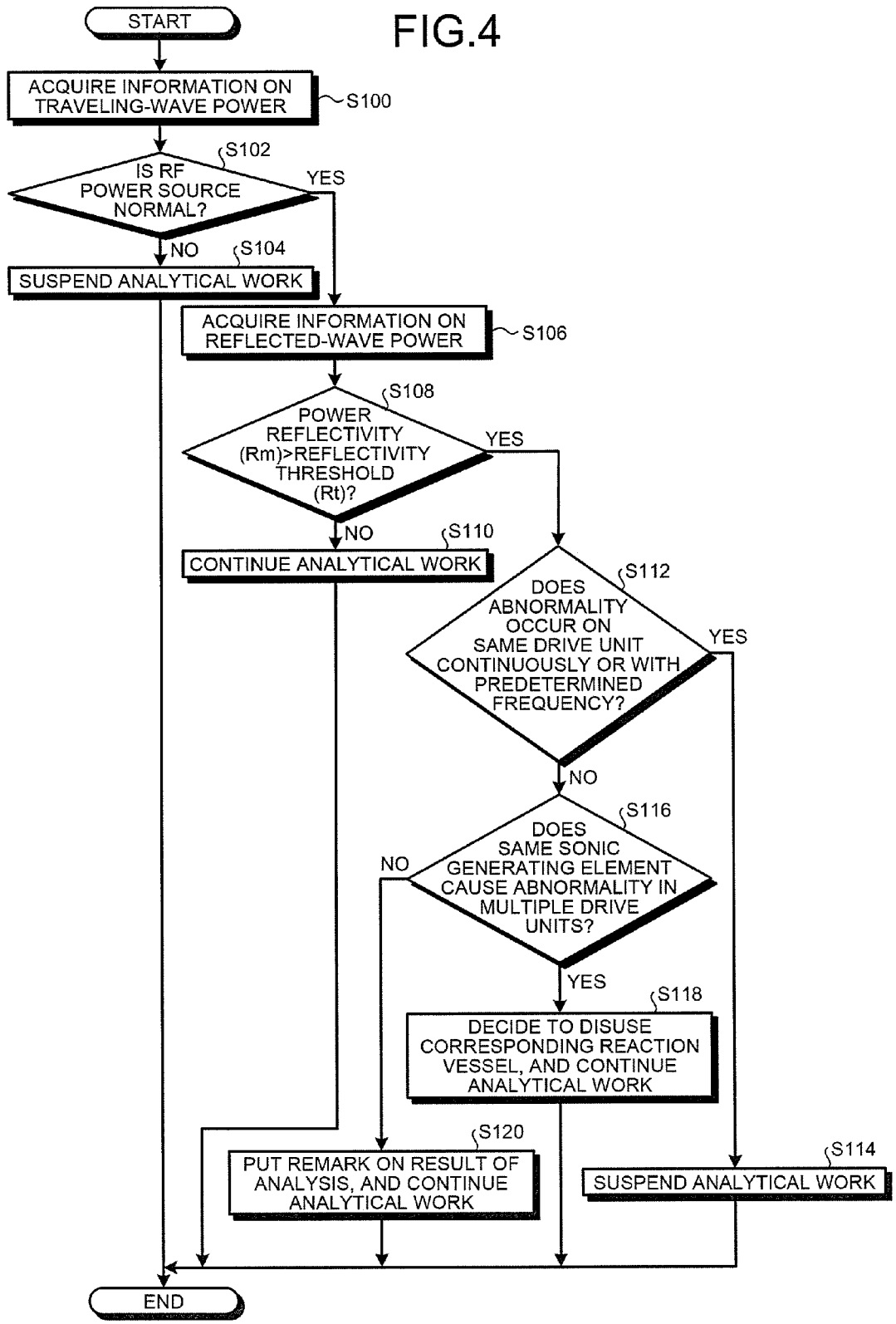
FIG. 4 is a flowchart illustrating a method for coping with an abnormality of the automatic analyzer according to the first embodiment.

The control unit 15 determines the presence or absence of an abnormality in each of the stirrers, specifically, on the side of the sound-wave generating element 23 or on the side of the drive unit 22 based on a reflectivity of the electric power in each of the specimen stirrer 20 and the reagent stirrers 26 and 27. The control unit 15 controls the continuation or suspension of the analytical work by the automatic analyzer 1 based on a result of the determination of the presence or absence of an abnormality in these. A process of coping with an abnormality of the automatic analyzer 1 executed by the control unit 15 is explained below with reference to a flowchart shown in FIG. 4. The abnormality coping process is preliminarily stored in the control unit 15 in the form of an abnormality coping program in consideration of situations of the occurrence of various possible abnormalities.

First, the control unit 15 acquires information on traveling-wave power of each stirrer from information input from the power detecting unit 24 of the stirrer to the determining unit 16 (Step S100). Then, the control unit 15 determines whether the RF power source 22e of the stirrer operates normally (Step S102). This determination is made depending on whether traveling-wave power input from the directional coupler 24a to the traveling-wave-power measuring circuit 24b is equal to or higher than a predetermined value. The RF power source 22e is determined to be normal when the traveling-wave power is equal to or higher than the predetermined value, and determined to be abnormal when the traveling-wave power is lower than the predetermined value.

As a result of the determination, when the RF power source 22e is abnormal (No at Step S102), the control unit 15 sets the suspension of the analytical work (Step S104). Then, the control unit 15 displays a message on the display unit 18 that the stirrer including the RF power source 22e determined to be abnormal is to be checked in order to announce this.

In contrast, when the RF power source 22e is normal (Yes at Step S102), the control unit 15 acquires information on reflected-wave power of the stirrer (Step S106). Then, the control unit 15 calculates a power reflectivity (Rm) based on the reflected-wave-power information and the previously-acquired traveling-wave-power information, and determines whether the power reflectivity (Rm) exceeds the reflectivity threshold (Rt=10%) (Step S108). When the power reflectivity (Rm) does not exceed the reflectivity threshold (Rt=10%) (No at Step S108), it can be considered that both the drive unit 22 side and the sound-wave generating element 23 side are normal. Thus, the control unit 15 continues the analysis (Step S110).

In contrast, when the power reflectivity (Rm) exceeds the reflectivity threshold (Rt=10%) (Yes at Step S108), the control unit 15 determines whether this situation arises on the side of the same drive unit 22 continuously or with predetermined frequency (Step S112). If it arises continuously or with predetermined frequency (Yes at Step S112), it can be considered that an abnormality occurs on the side of the drive unit 22 (for example, a bad connection or an overflow of liquid from the reaction vessel 5 occurs). Consequently, the control unit 15 suspends the analytical work (Step S114). At the same time, the control unit 15 displays a maintenance request for an operator on the display unit 18 in order to announce the abnormality. As the predetermined frequency, for example, more than 2 times per 10 measurements shall be the reference.

In contrast, if it does not arise continuously or with predetermined frequency (No at Step S112), the control unit 15 determines whether the same sound-wave generating element 23 causes an abnormality in plural drive units 22 (Step S116). As a result of the determination, if the same sound-wave generating element 23 causes an abnormality in the plural drive units 22 (Yes at Step S116), the control unit 15 decides to disuse the reaction vessel 5 on which this sound-wave generating element 23 is mounted, and continues the analytical work (Step S118). As a result of the determination, if the same sound-wave generating element 23 does not cause an abnormality over plural drive units 22 (No at Step S116), the abnormality can be considered as a temporary abnormality on the side of the drive unit 22 or on the side of the sound-wave generating element 23. Thus, the control unit 15 puts a remark calling for attention on a result of the analysis, and continues the analytical work (Step S120).

In the abnormality coping process for the automatic analyzer 1 described above, the analytical work is continued if there is no abnormality, and the analytical work is suspended if there is an abnormality. By the announcement concerning the abnormality on the side of the drive units 22 or on the side of the sound-wave generating element 23 through the display on the display unit 18, an operator copes with the abnormality by checking the connection between the drive unit 22 and the sound-wave generating element 23, replacing the reaction vessel 5 with a new one, replacing a component with a new one, or the like; cancels the error status; and restarts the automatic analyzer 1, so that the analytical work can be resumed.

As described above, according to the analyzer and its abnormality coping method of the first embodiment, even when an abnormality occurs with the stirrer, an analytical work is not suspended across the board, and thus it is possible to suppress the decrease in efficiency of treating specimens. If an abnormality check menu is provided in a control menu of the control unit 15 so that a user can personally cope with an abnormality, the automatic analyzer 1 can shorten the downtime, and further improve the efficiency of examination.

Second Embodiment

Figure 5:
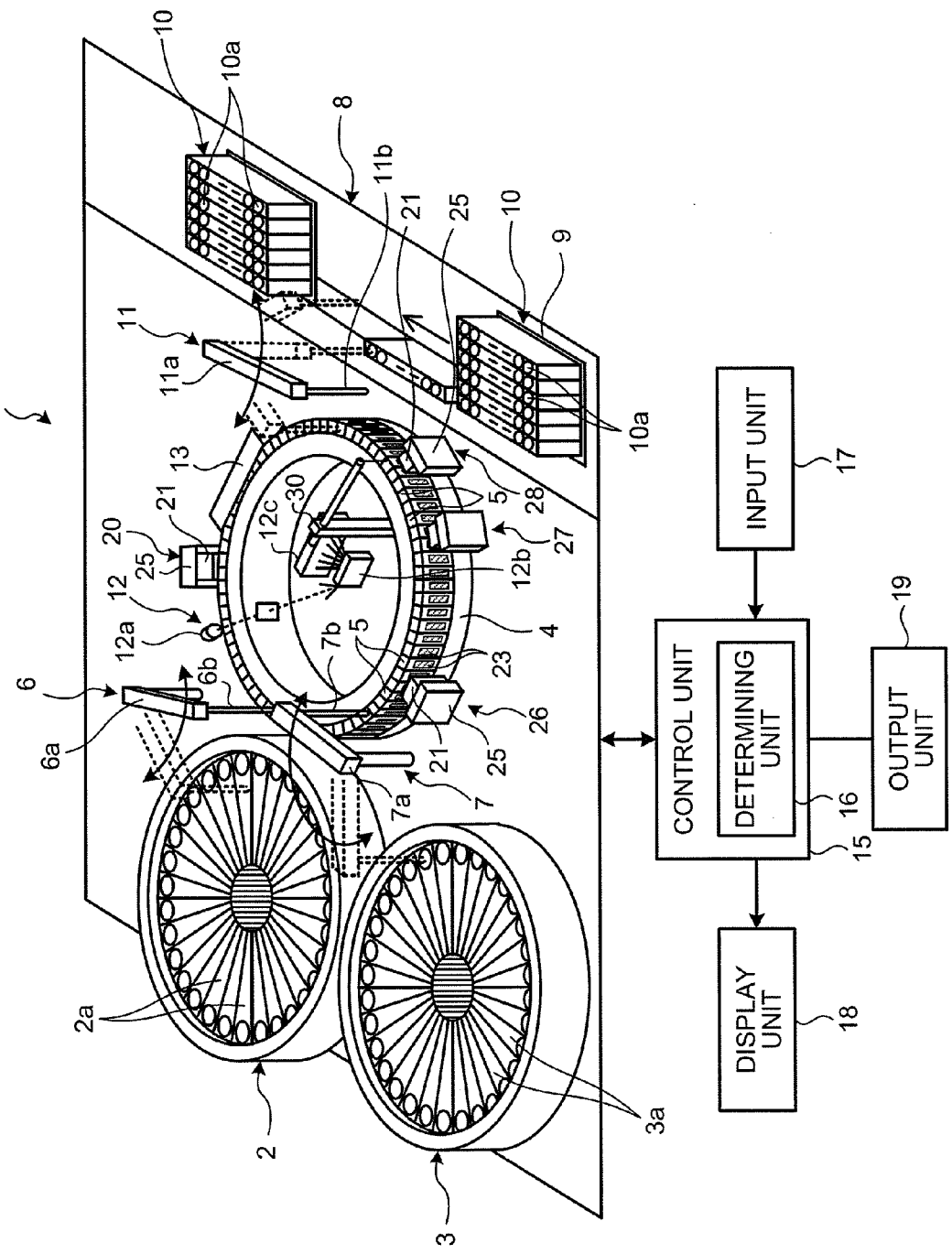
FIG. 5 is a schematic configuration diagram illustrating an automatic analyzer according to a second embodiment.
Figure 6:
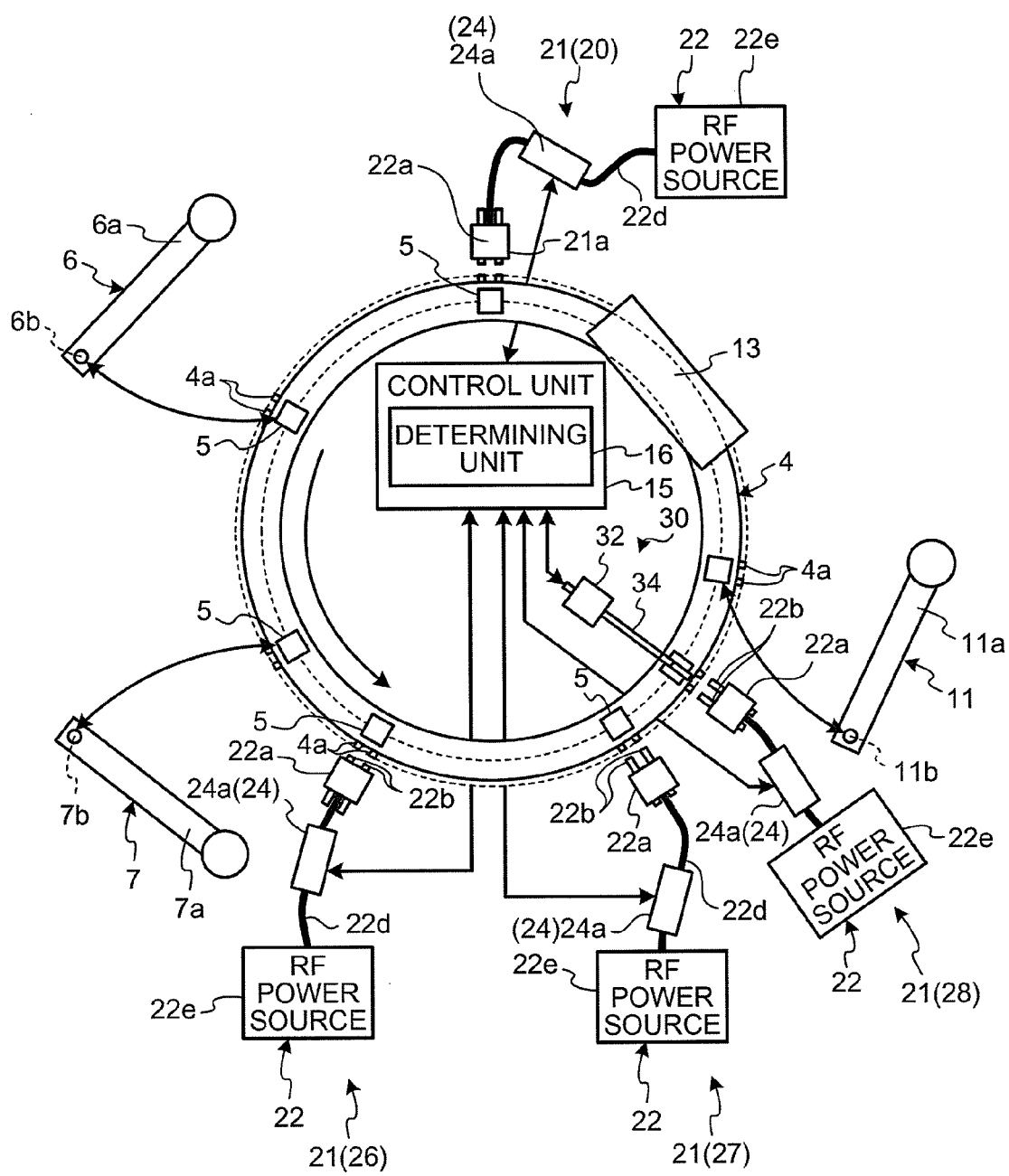
FIG. 6 is a plan view illustrating the reagent dispensing system, the specimen dispensing system, the specimen stirrer, the reagent stirrer, a determination stirrer, and a temperature measuring device that are arranged near the reaction table in the automatic analyzer according to the second embodiment.

Subsequently, a second embodiment of an analyzer and its abnormality coping method of the present invention will be described in detail below with reference to the accompanying drawings. In the first embodiment, the presence or absence of an abnormality is determined using the power detecting unit. In the second embodiment, the presence or absence of an abnormality is determined using a temperature detecting unit and the power detecting unit. FIG. 5 is a schematic configuration diagram illustrating an automatic analyzer according to the second embodiment. FIG. 6 is a plan view illustrating the reagent dispensing system, the specimen dispensing system, the specimen stirrer, the reagent stirrer, a determination stirrer, and a temperature measuring device that are arranged near the reaction table in the automatic analyzer according to the second embodiment. An automatic analyzer 40 according to the second embodiment has the same configuration as the automatic analyzer 1 according to the first embodiment except that the automatic analyzer 40 is provided with a determination stirrer 28 and a temperature measuring device 30. Thus, the same components are denoted by the same reference numerals.

As shown in FIGS. 5 and 6, the automatic analyzer 40 includes the reagent tables 2 and 3, the reaction table 4, the specimen-vessel transfer system 8, the analysis optical system 12, the cleaning system 13, the control unit 15, the specimen stirrer 20, the power detecting unit 24, the reagent stirrers 26 and 27, the determination stirrer 28, and the temperature measuring device 30.

The control unit 15 controls the start or suspension of an analytical work based on the presence or absence of an abnormality of each of the stirrers determined by the determining unit 16. The determining unit 16 determines the presence or absence of an abnormality of each of the stirrers based on a reflectivity of the electric power in each of the specimen stirrer 20, the reagent stirrers 26 and 27, and the determination stirrer 28 detected by the power detecting unit 24 or a change in temperature of liquid at least before and after being stirred measured by the temperature measuring device 30.

The determination stirrer 28 is a stirrer used when the temperature measuring device 30 detects the temperature of liquid after the stirring with sound wave, and is arranged between the cleaning system 13 and the reagent stirrer 27 on the outer circumference of the reaction table 4. The determination stirrer 28 has the same configuration as the specimen stirrer 20 and the reagent stirrers 26 and 27, and includes the stirring unit 21 and the positioning member 25.

Figure 7:
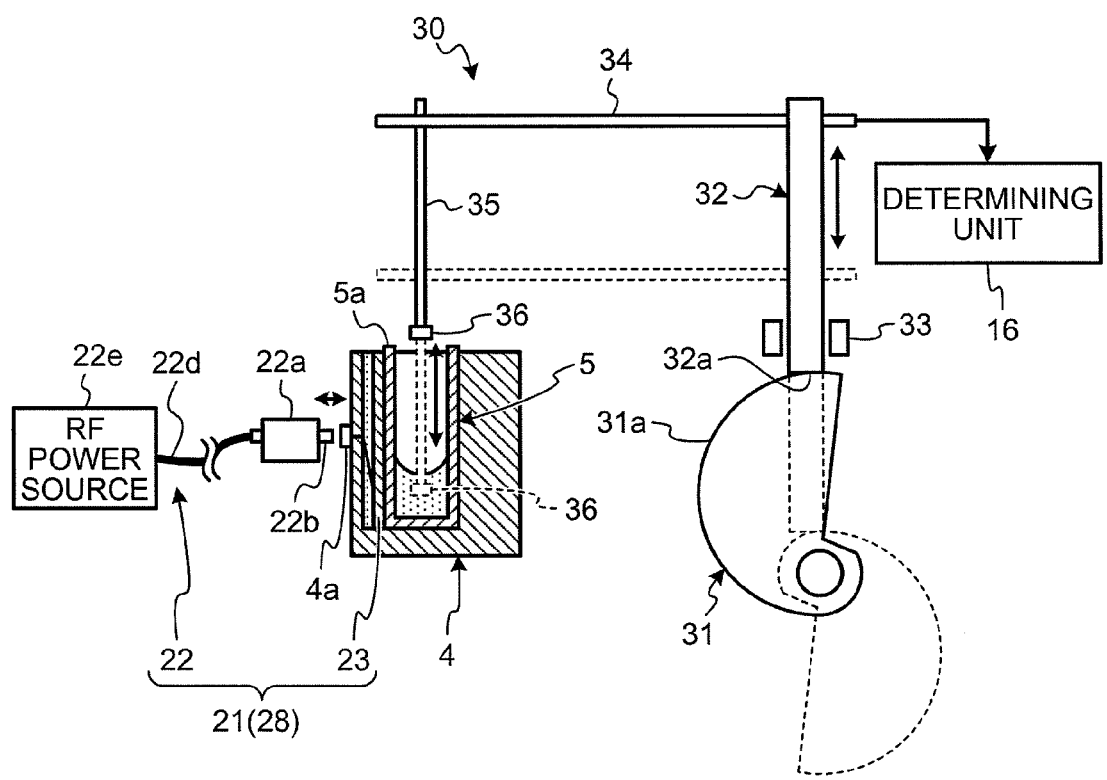
FIG. 7 is a diagram illustrating schematic configurations of the determination stirrer and the temperature measuring device together with a cross-section of the reaction table holding a reaction vessel.

The temperature measuring device 30 detects the temperature of the liquid after the stirring with sound wave generated by the sound-wave generating element 23, and as shown in FIGS. 5, 6, and 7, is arranged at the position opposed to the determination stirrer 28 across the reaction table 4, and includes a temperature sensor 36. Specifically, the temperature measuring device 30 detects an abnormality arising from the poor adhesion or detachment of the sound-wave generating element 23 to or from the reaction vessel 5 from a temperature change of the liquid. As the liquid used for the detection of the temperature change, cleaning water used by the cleaning system 13 to clean the reaction vessel 5 is used.

The temperature sensor 36 is provided at the lower end of a supporting member 35, and measures the temperature of liquid held in the reaction vessel 5. For example, a thermistor or a thermocouple may be used. The supporting member 35 is supported by an arm 34 provided on a bracing strut 32 that is moved up and down by rotation of a cam 31. The cam 31 is turned by a drive means (not shown) such as a motor. A stepped portion 32a with which a cam surface 31a of the cam 31 is in contact is formed on the middle of the bracing strut 32, and the up-and-down movement of the bracing strut 32 is smoothly guided by a guide member 33.

The determining unit 16 determines the presence or absence of an abnormality on the side of each of the sound-wave generating elements 23 based on the temperature of liquid detected by the temperature measuring device 30. For example, if a difference in temperature of the liquid before and after being stirred ($\Delta T$) is equal to or lower than a temperature-difference threshold ($\Delta Tt$) ($\Delta T \leq \Delta Tt$), the determining unit 16 determines that there is an abnormality on the side of the sound-wave generating element 23. In making determination using a temperature change, various means, such as time change in temperature, can be used. Thus, in addition to an abnormality on the side of the sound-wave generating element 23 detected by the power detecting unit 24, the poor adhesion of the sound-wave generating element 23 to the reaction vessel 5 can be detected using the temperature measuring device 30.

The automatic analyzer 40 configured as described above operates under the control of the control unit 15. A first reagent, a specimen, and a second reagent are dispensed into the reaction vessels 5, which are conveyed along the circumferential direction by the rotating reaction table 4, in this order by the reagent dispensing systems 6 and 7 and the specimen dispensing system 11, respectively. The dispensed reagents and specimen are stirred by the reagent stirrers 26 and 27 and the specimen stirrer 20 sequentially.

Then, when each of the reaction vessels 5 in which the reagents and the specimen have been stirred passes through the analysis optical system 12, an optical property of the reaction liquid is measured in the light-receiving unit 12c, and the component concentration and the like are analyzed by the control unit 15. The reaction vessel 5 that has undergone the light measurement of the reaction liquid is cleaned by the cleaning system 13, and then used for analysis of a specimen again.

When the reaction vessel 5 is cleaned after completion of the analysis, a certain amount of cleaning water is discharged from the cleaning system 13 into each reaction vessel 5. The control unit 15 then causes the determination stirrer 28 to stir the certain amount of cleaning water dispensed into each reaction vessel 5 and also causes the temperature measuring device 30 to measure a temperature change in accordance with the stirring of the cleaning water by the determination stirrer 28.

Then, the control unit 15 determines the presence or absence of an abnormality in each of the stirrers, specifically, on the side of the sound-wave generating element 23 or on the side of the drive unit 22 based on any of the temperature change in accordance with the stirring of the cleaning water by the determination stirrer 28 and a reflectivity of the electric power in each of the specimen stirrer 20 and the reagent stirrers 26 and 27 or a combination of these. The control unit 15 controls the continuation or suspension of the analytical work by the automatic analyzer 40 based on a result of the determination of the presence or absence of an abnormality. A process of coping with an abnormality of the automatic analyzer 40 executed by the control unit 15 is explained below with reference to a flowchart shown in FIG. 8. The abnormality coping process is preliminarily stored in the control unit 15 in the form of an abnormality coping program in consideration of situations of the occurrence of various possible abnormalities.

First, the control unit 15 acquires information on traveling-wave power of each stirrer from information input from the power detecting unit 24 of the stirrer to the determining unit 16 (Step S200). Then, the control unit 15 determines whether the RF power source 22e of the stirrer operates normally (Step S202). This determination is made depending on whether traveling-wave power input from the directional coupler 24a to the traveling-wave-power measuring circuit 24b is equal to or higher than a predetermined value. The RF power source 22e is determined to be normal when the traveling-wave power is equal to or higher than the predetermined value and determined to be abnormal when the traveling-wave power is lower than the predetermined value.

As a result of the determination, when the RF power source 22e is abnormal (No at Step S202), the control unit 15 sets the suspension of the analytical work (Step S204). Then, the control unit 15 displays a message on the display unit 18 that the stirrer including the RF power source 22e determined to be abnormal is to be checked in order to announce this.

In contrast, when the RF power source 22e is normal (Yes at Step S202), the control unit 15 acquires information on the temperature of cleaning water before and after being stirred based on information input from the temperature measuring device 30 (Step S206). Then, the control unit 15 causes the determining unit 16 to determine whether a difference in temperature of the cleaning water before and after being stirred ($\Delta T$) is equal to or lower than the temperature-difference threshold ($\Delta Tt$) based on a change in the acquired temperatures of the cleaning water before and after being stirred (Step S208).

If the temperature difference ($\Delta T$) is equal to or lower than the temperature-difference threshold ($\Delta Tt$) (Yes at Step S208), the control unit 15 determines whether this situation arises continuously or with predetermined frequency (Step S210). When the temperature difference ($\Delta T$) is equal to or lower than the temperature-difference threshold ($\Delta Tt$), it can be considered that an abnormality occurs; however, how to cope with the abnormality differs depending on a situation of the occurrence of the abnormality. As the predetermined frequency, for example, more than 2 times per 10 temperature measurements shall be the reference. Then, if such a situation arises in the different reaction vessel 5 continuously or with predetermined frequency (Yes at Step S210), it can be considered that an abnormality occurs on the side of the drive unit 22 of the determination stirrer 28 (for example, a bad connection or an overflow of liquid from the reaction vessel 5 occurs). Consequently, the control unit 15 suspends the analytical work (Step S212). At the same time, the control unit 15 displays a maintenance request for an operator on the display unit 18 in order to announce the abnormality.

In contrast, if another case (No at Step S210), it can be considered that an abnormality occurs on the side of the sound-wave generating element 23. Consequently, the control unit 15 decides to disuse the reaction vessel 5 on which this sound-wave generating element 23 is mounted, and continues the analytical work (Step S214). At the same time, the control unit 15 displays on the display unit 18 a maintenance request for the reaction vessel 5 decided to be disused for an operator in order to announce the abnormality.

In contrast, if the temperature difference (ΔT) exceeds the temperature-difference threshold (ΔTt) (No at Step S208), it can be considered that the side of the drive unit 22 of the determination stirrer 28 is normal. Consequently, the control unit 15 further acquires information on reflected-wave power of the stirrer (Step S216). Then, the control unit 15 calculates a power reflectivity (Rm) based on the reflected-wave-power information and the previously-acquired traveling-wave-power information, and determines whether the power reflectivity (Rm) exceeds the reflectivity threshold (Rt=10%) (Step S218). If the power reflectivity (Rm) does not exceed the reflectivity threshold (Rt=10%) (No at Step S218), it can be considered that both the drive unit 22 side and the sound-wave generating element 23 side are normal. Thus, the control unit 15 continues the analysis (Step S220).

In contrast, if the power reflectivity (Rm) exceeds the reflectivity threshold (Rt=10%) (Yes at Step S218), the control unit 15 determines whether this situation arises on the side of the same drive unit 22 at the different reaction vessels 5 continuously or with predetermined frequency (Step S222). If it arises continuously or with predetermined frequency (Yes at Step S222), it can be considered that an abnormality occurs on the side of the drive unit 22 of the determination stirrer 28 (for example, a bad connection or an overflow of liquid from the reaction vessel 5 occurs). Consequently, the control unit 15 suspends the analytical work (Step S224). At the same time, the control unit 15 displays on the display unit 18 a maintenance request for an operator in order to announce the abnormality. As the predetermined frequency, for example, more than 2 times per 10 measurements shall be the reference.

In contrast, if it does not arise continuously or with predetermined frequency (No at Step S222), the control unit 15 determines whether the same sound-wave generating element 23 causes an abnormality over plural drive units 22 (Step S226). As a result of the determination, if the same sound-wave generating element 23 causes an abnormality over plural drive units 22 (Yes at Step S226), it can be considered that this sound-wave generating element 23 has some kind of abnormality. Consequently, the control unit 15 decides to disuse the reaction vessel 5 on which this sound-wave generating element 23 is mounted, and continues the analytical work (Step S228). As a result of the determination, if the same sound-wave generating element 23 does not cause an abnormality over plural drive units 22 (No at Step S226), the abnormality can be considered as a temporary abnormality on the side of the drive unit 22 or on the side of the sound-wave generating element 23. Thus, the control unit 15 puts a remark calling for attention on a result of the analysis, and continues the analytical work (Step S230).

In the abnormality coping process for the automatic analyzer 40 described above, the analytical work is continued if there is no abnormality, and the analytical work is suspended if there is an abnormality. By the announcement concerning the abnormality on the side of the drive unit 22 or on the side of the sound-wave generating element 23 through the display on the display unit 18, an operator copes with the abnormality by checking the connection between the drive unit 22 and the sound-wave generating element 23, replacing the reaction vessel 5 with a new one, replacing a component with a new one, or the like; cancels the error status; and restarts the automatic analyzer 40, so that the analytical work can be resumed.

As described above, according to the analyzer and its abnormality coping method of the second embodiment, even when an abnormality occurs with the stirrer, an analytical work is not suspended across the board, and thus it is possible to suppress the decrease in efficiency of treating specimens. If an abnormality check menu is set up in a control menu of the control unit 15 so that a user can personally cope with an abnormality, the automatic analyzer 40 can shorten the downtime and further improve the efficiency of examination.

Incidentally, the analyzer and its abnormality coping method of the present invention can be configured to determine the presence or absence of an abnormality on the side of the sound-wave generating element of each of the stirrers based only on a temperature change of the liquid before and after being stirred and to control the continuation or suspension of the analytical work based on a result of the determination.

Furthermore, the abnormality coping process for the analyzer described above can be executed at a timing before the start of analysis by the automatic analyzer 1 or 40, during the analysis, or after completion of the analysis.

Moreover, there is described a case where the automatic analyzer explained in the embodiments includes one reaction table 4, i.e., one analyzing unit; however, a plurality of analyzing units can be arranged in the automatic analyzer. Furthermore, there is described a case where the automatic analyzer includes two reagent tables for the first reagent and the second reagent; however, the automatic analyzer can include one reagent table.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An analyzer comprising:
  a plurality of a sound-wave generating units, wherein each of the sound-wave generating units is provided on a vessel that can hold a liquid, and wherein each of the sound-wave generating unit generates a sound wave toward the liquid that stirs the liquid;
  a plurality of stirring units, each of the stirring units comprising:
    a drive unit and
    a power detecting unit,
  wherein the drive unit comprises a power source and drives the sound-wave generating units, wherein the power detecting unit detects a traveling-wave power output from the power source and a reflected-wave power reflected from the sound-wave generating units, wherein the number of the sound-wave generating units is greater than the number of the stirring units, and wherein the sound-wave generating units and the drive units make up a plurality of stirrers, each stirrer being one drive unit and one sound-wave generating unit;
  a control unit that makes a power abnormality determination on whether an abnormality occurs in each of the plurality of stirrers from a drive unit or from a sound-wave generating unit, wherein the power abnormality determination is based on a ratio between the traveling-wave power and the reflected wave power, and wherein the control unit sets a continuation or a suspension of an analytical work based on the power abnormality determination; and a temperature detecting unit that detects a temperature of the liquid, wherein the control unit makes a temperature abnormality determination on whether an abnormality occurs in each of the plurality of stirrers from a drive unit or from a sound-wave generating unit, wherein the temperature abnormality determination is based on a change in temperature of the liquid before and after being stirred, wherein the control unit sets a continuation or a suspension of an analytical work based on the temperature abnormality determination.

2. The analyzer according to claim 1, wherein when an abnormality occurs in the stirrers from a specific sound-wave generating unit, the control unit sets to disuse a vessel provided with the specific sound-wave generating unit and sets a continuation of an analytical work for other vessels.

3. The analyzer according to claim 2, further comprising an announcing unit that announces the abnormality that occurs in the stirrers from the specific sound-wave generating unit, wherein the control unit displays a warning calling attention to an analysis result or causes the announcing unit to announce the abnormality that occurs in the stirrers from the specific sound-wave generating unit.

4. The analyzer according to claim 3, wherein when an abnormality occurs in the stirrers from a drive unit, the control unit sets a suspension of an analytical work and informs the announcing unit that a stirrer needs to be checked.

5. The analyzer according to claim 1, the temperature detecting unit comprises a temperature sensor, wherein the temperature sensor is a thermistor or a thermocouple.

6. A method for coping with an abnormality, the method comprising:
(a) providing an analyzer comprising:
  a plurality of a sound-wave generating units, wherein each of the sound-wave generating units is provided on a vessel holding a liquid, and wherein each of the sound-wave generating units generates a sound wave toward the liquid that stirs the liquid;
  a plurality of stirring units, each of the stirring units comprising:
    a drive unit and
    a power detecting unit,
  wherein the drive unit comprises a power source and drives the sound-wave generating units, wherein the number of the sound-wave generating units is greater than the number of the stirring units, and wherein the sound-wave generating units and the drive units make up a plurality of stirrers, each stirrer being one drive unit and one sound-wave generating unit;
(b) detecting a traveling-wave power output from the power source and a reflected wave power reflected from the sound-wave generating units with the power detecting unit;
(c) making a power abnormality determination on whether an abnormality occurs in each of the plurality of stirrers from a drive unit or from a sound-wave generating unit, wherein the power abnormality determination is based on a ratio between the traveling-wave power and the reflected wave power;
(d) detecting a change in a temperature of the liquid before and after being stirred;
(e) making a temperature abnormality determination on whether an abnormality occurs in each of the plurality of stirrers from a drive unit or from a sound-wave generating unit, wherein the temperature abnormality determination is based on the change in the temperature of the liquid before and after being stirred; and
(f) setting a continuation or a suspension of an analytical work based on the power abnormality determination and the temperature abnormality determination.

* * * * *